(12) United States Patent
Lieu (10) Patent No.: US 11,154,421 B2
(45) Date of Patent: Oct. 26, 2021

(54) SYSTEM AND METHOD FOR PROVIDING PRESSURIZED INFUSION TRANSFER RESERVOIRS

(71) Applicant: JOHNSON & JOHNSON SURGICAL VISION, INC., Santa Ana, CA (US)

(72) Inventor: Katrina T. Lieu, Irvine, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 381 days.

(21) Appl. No.: 15/959,020

(22) Filed: Apr. 20, 2018

(65) Prior Publication Data
US 2019/0321222 A1 Oct. 24, 2019

(51) Int. Cl.
*A61F 9/007* (2006.01)
*A61M 39/28* (2006.01)
*A61M 1/00* (2006.01)

(52) U.S. Cl.
CPC ............ *A61F 9/00736* (2013.01); *A61M 1/77* (2021.05); *A61M 1/774* (2021.05); *A61M 39/288* (2013.01); *A61B 2217/007* (2013.01); *A61M 2205/3331* (2013.01); *A61M 2210/0612* (2013.01)

(58) Field of Classification Search
CPC ............ A61F 9/00736; A61M 3/0237; A61M 3/0233; A61M 39/288
See application file for complete search history.

(56) References Cited

U.S. PATENT DOCUMENTS

| 1,455,235 | A | | 5/1923 | Townsend et al. |
| 2,208,550 | A | | 7/1940 | Shapiro |
| 2,373,124 | A | | 4/1945 | Frank |
| 2,413,710 | A | | 1/1947 | Jason |
| 2,542,461 | A | * | 2/1951 | Bay ................... A61M 3/0241 604/128 |

(Continued)

FOREIGN PATENT DOCUMENTS

| EP | 1356834 A2 | 10/2003 |
| EP | 1428541 A2 | 6/2004 |

(Continued)

OTHER PUBLICATIONS

Partial International Search Report for Application No. PCT/IB2019/053136, dated Aug. 5, 2010, 17 pages.

*Primary Examiner* — Jenna Zhang
(74) *Attorney, Agent, or Firm* — Johnson & Johnson Surgical Vision, Inc.

(57) ABSTRACT

Apparatus, system and method for providing pressurized infusion of liquids and, more particularly, providing a stable and pressurized flow of fluid to the eye during surgery. Aspiration fluid may be received via an aspiration line at a first peristaltic pump, where aspiration fluid is transferred to a Venturi tank reservoir coupled to a second peristaltic pump. Fluid from a fluid source is provided via a third peristaltic pump to a pressurized infusion tank. A determination is made if the pressure in the pressurized infusion tank is at a predetermined level, where fluid may be transferred from the pressurized infusion tank to an irrigation line when pressure in the pressurized infusion tank is determined to be at the predetermined level. Alternate activation of a plurality of aspiration and irrigation lines are also provided.

12 Claims, 4 Drawing Sheets

(56) References Cited

U.S. PATENT DOCUMENTS

| | | | |
|---|---|---|---|
| 2,716,517 A | 8/1955 | Tollberg | |
| 2,844,351 A * | 7/1958 | Smith | A61M 39/28 251/4 |
| 2,954,806 A | 10/1960 | Kerr | |
| 3,693,613 A | 9/1972 | Kelman | |
| 3,812,855 A | 5/1974 | Banko | |
| 3,838,691 A | 10/1974 | Paludan et al. | |
| 3,931,818 A | 1/1976 | Goldowsky | |
| 3,973,602 A | 8/1976 | Kruse | |
| 4,052,987 A | 10/1977 | Wuchinich et al. | |
| 4,156,187 A | 5/1979 | Brumbach et al. | |
| 4,180,074 A | 12/1979 | Murry et al. | |
| 4,186,848 A | 2/1980 | Walter | |
| 4,221,308 A | 9/1980 | Goodall | |
| 4,292,969 A * | 10/1981 | Raible | A61M 39/288 251/340 |
| 4,328,803 A * | 5/1982 | Pape | A61F 9/00781 604/28 |
| 4,343,824 A | 8/1982 | Caldwell | |
| 4,361,148 A * | 11/1982 | Shackleford | A61J 1/10 604/410 |
| 4,425,123 A | 1/1984 | Di Salvo | |
| 4,548,205 A | 10/1985 | Armeniades et al. | |
| 4,570,898 A * | 2/1986 | Staeubli | A61M 39/288 251/4 |
| 4,620,564 A * | 11/1986 | Ekholmer | A61M 5/16881 137/595 |
| 4,813,927 A | 3/1989 | Morris et al. | |
| 4,832,685 A | 5/1989 | Haines | |
| 4,841,984 A | 6/1989 | Armeniades et al. | |
| 4,900,301 A | 2/1990 | Morris et al. | |
| 4,921,477 A | 5/1990 | Davis | |
| 4,926,856 A | 5/1990 | Cambio, Jr. et al. | |
| 5,032,111 A | 7/1991 | Morris et al. | |
| 5,047,009 A | 9/1991 | Morris et al. | |
| 5,112,019 A | 5/1992 | Metzler et al. | |
| 5,176,629 A | 1/1993 | Kullas et al. | |
| 5,234,038 A | 8/1993 | Mitchell et al. | |
| 5,242,404 A | 9/1993 | Conley et al. | |
| 5,246,422 A | 9/1993 | Favre | |
| 5,341,836 A | 8/1994 | Doherty | |
| 5,342,293 A | 8/1994 | Zanger | |
| 5,360,398 A * | 11/1994 | Grieshaber | A61M 3/0208 604/30 |
| 5,403,276 A | 4/1995 | Schechter et al. | |
| 5,417,246 A | 5/1995 | Perkins et al. | |
| 5,429,601 A | 7/1995 | Conley et al. | |
| 5,563,584 A | 10/1996 | Rader et al. | |
| 5,593,385 A | 1/1997 | Harrison et al. | |
| 5,593,392 A * | 1/1997 | Starchevich | A61M 39/284 251/4 |
| 5,624,394 A | 4/1997 | Barnitz et al. | |
| 5,649,905 A | 7/1997 | Zanger et al. | |
| 5,676,650 A | 10/1997 | Grieshaber et al. | |
| 5,697,898 A | 12/1997 | Devine | |
| 5,700,240 A | 12/1997 | Barwick, Jr. et al. | |
| 5,733,256 A | 3/1998 | Costin | |
| 5,766,146 A | 6/1998 | Barwick, Jr. | |
| 5,795,328 A | 8/1998 | Barnitz et al. | |
| 5,810,765 A | 9/1998 | Oda | |
| 5,830,176 A | 11/1998 | MacKool | |
| 5,865,764 A | 2/1999 | Moorhead | |
| 5,910,110 A | 6/1999 | Bastable | |
| 5,954,971 A | 9/1999 | Pages et al. | |
| 6,013,049 A | 1/2000 | Rockley et al. | |
| 6,024,720 A | 2/2000 | Chandler et al. | |
| 6,083,193 A | 7/2000 | Kadziauskas et al. | |
| 6,149,621 A | 11/2000 | Makihara | |
| 6,159,175 A | 12/2000 | Strukel et al. | |
| 6,179,808 B1 | 1/2001 | Boukhny et al. | |
| 6,241,700 B1 | 6/2001 | Leukanech | |
| 6,261,283 B1 | 7/2001 | Morgan et al. | |
| 6,261,297 B1 | 7/2001 | Kadziauskas et al. | |
| 6,280,408 B1 | 8/2001 | Sipin | |
| 6,283,937 B1 | 9/2001 | Takamatsu et al. | |
| 6,290,690 B1 | 9/2001 | Huculak et al. | |
| 6,391,000 B1 | 5/2002 | Belikan et al. | |
| 6,491,661 B1 | 12/2002 | Boukhny et al. | |
| 6,511,454 B1 | 1/2003 | Nakao et al. | |
| 6,527,745 B1 | 3/2003 | Kanda et al. | |
| 6,730,106 B2 | 5/2004 | Kanda et al. | |
| 6,780,166 B2 | 8/2004 | Kanda et al. | |
| 6,849,059 B2 | 2/2005 | Suzuki et al. | |
| 6,875,194 B2 | 4/2005 | MacKool | |
| 6,899,694 B2 | 5/2005 | Kadziauskas et al. | |
| 6,908,451 B2 | 6/2005 | Brody et al. | |
| 6,969,032 B2 | 11/2005 | Olivera et al. | |
| 6,997,896 B2 | 2/2006 | Novak | |
| 7,001,356 B2 | 2/2006 | Kadziauskas et al. | |
| 7,018,355 B2 | 3/2006 | Kadziauskas et al. | |
| 7,197,567 B1 | 3/2007 | Fitzgerald | |
| 7,563,242 B2 | 7/2009 | Yaguchi et al. | |
| 7,867,191 B2 | 1/2011 | Suzuki | |
| 7,967,777 B2 | 6/2011 | Edwards et al. | |
| 8,070,712 B2 | 12/2011 | Muri et al. | |
| 8,287,486 B2 | 10/2012 | Injev | |
| 8,388,582 B2 | 3/2013 | Eubanks et al. | |
| 8,679,089 B2 | 3/2014 | Berlin | |
| 9,205,186 B2 | 12/2015 | Tarkeshian et al. | |
| 9,433,723 B2 | 9/2016 | Steen et al. | |
| 9,445,943 B2 | 9/2016 | Wilson et al. | |
| 9,511,184 B2 | 12/2016 | Woolford et al. | |
| 10,729,581 B2 | 8/2020 | Boukhny et al. | |
| 2001/0004684 A1 | 6/2001 | Morgan et al. | |
| 2001/0023331 A1 | 9/2001 | Kanda et al. | |
| 2002/0019601 A1 | 2/2002 | Wada | |
| 2002/0019607 A1 | 2/2002 | Bui | |
| 2002/0085952 A1 | 7/2002 | Ellingboe et al. | |
| 2003/0163138 A1 | 8/2003 | Nazarifar et al. | |
| 2003/0201412 A1 | 10/2003 | Brody et al. | |
| 2004/0108340 A1 | 6/2004 | Witt | |
| 2004/0116846 A1 | 6/2004 | Olivera et al. | |
| 2005/0237503 A1 | 10/2005 | Kubo | |
| 2006/0100580 A1 | 5/2006 | Muller | |
| 2006/0149301 A1 | 7/2006 | Claus | |
| 2008/0033349 A1 | 2/2008 | Suzuki | |
| 2008/0114290 A1 | 5/2008 | King et al. | |
| 2010/0145302 A1 | 6/2010 | Cull et al. | |
| 2010/0280434 A1 | 11/2010 | Raney et al. | |
| 2010/0280435 A1 | 11/2010 | Raney et al. | |
| 2010/0292631 A1 | 11/2010 | Holden et al. | |
| 2011/0054385 A1 | 3/2011 | Eichler | |
| 2011/0112472 A1 | 5/2011 | Jacobson et al. | |
| 2011/0282273 A1 | 11/2011 | Evans et al. | |
| 2011/0295191 A1 | 12/2011 | Injev | |
| 2011/0313343 A1 | 12/2011 | Milutinovic et al. | |
| 2012/0215160 A1 | 8/2012 | Valenti et al. | |
| 2012/0232466 A1 | 9/2012 | Kuebler et al. | |
| 2013/0131578 A1 | 5/2013 | Stalmans et al. | |
| 2013/0138035 A1 | 5/2013 | Huculak et al. | |
| 2013/0237900 A1 | 9/2013 | Hauger | |
| 2013/0245543 A1 | 9/2013 | Gerg et al. | |
| 2013/0267779 A1 | 10/2013 | Woolford et al. | |
| 2014/0074013 A1 | 3/2014 | McCary et al. | |
| 2014/0114237 A1 | 4/2014 | Gordon et al. | |
| 2014/0276639 A1 | 9/2014 | Tarkeshian et al. | |
| 2016/0095750 A1 | 4/2016 | Raney et al. | |
| 2016/0100981 A1 * | 4/2016 | Klomp | A61M 39/223 604/290 |
| 2016/0220751 A1 | 8/2016 | Mallough et al. | |
| 2017/0151090 A1 | 6/2017 | Raney et al. | |
| 2017/0151092 A1 | 6/2017 | Raney et al. | |
| 2017/0151376 A1 | 6/2017 | Raney et al. | |
| 2017/0151377 A1 | 6/2017 | Raney et al. | |
| 2017/0151378 A1 | 6/2017 | Raney et al. | |
| 2017/0151379 A1 | 6/2017 | Raney et al. | |
| 2017/0273826 A1 * | 9/2017 | Sanchez, Jr. | A61F 9/0017 |

FOREIGN PATENT DOCUMENTS

| | | |
|---|---|---|
| WO | 9112034 A1 | 8/1991 |
| WO | 9418894 A1 | 9/1994 |

(56) References Cited

FOREIGN PATENT DOCUMENTS

| WO | 0217833 | A1 | 3/2002 |
| WO | 2009112251 | A1 | 9/2009 |
| WO | 2012092018 | A1 | 7/2012 |

* cited by examiner

SYSTEM AND METHOD FOR PROVIDING PRESSURIZED INFUSION TRANSFER RESERVOIRS

BACKGROUND

Field of the Invention

The present invention relates generally to providing pressurized infusion of liquids and, more particularly, is directed to providing a stable and pressurized flow of irrigation fluid to the eye during surgery utilizing a transfer reservoir to accommodate a necessary amount of balanced salt solution from any type of balanced salt solution container.

Description of the Background

Certain surgical procedures, such as phacoemulsification surgery, have been successfully employed in the treatment of certain ocular problems, such as cataracts. Phacoemulsification surgery utilizes a small incision into the sclera or clear cornea to insert the tip of at least one phacoemulsification handheld surgical implement, or handpiece, through the corneal incision. The handpiece includes a needle which is ultrasonically driven once placed within the incision to emulsify the eye lens, or to break the cataract into small pieces. The broken cataract pieces or emulsified eye lens may subsequently be removed using the same handpiece, or another handpiece, in a controlled manner. The surgeon may then insert a lens implant into the eye through the incision. The incision is allowed to heal, and the result for the patient is typically significantly improved eyesight.

As may be appreciated, the flow of fluid to and from a patient through a fluid infusion or extraction system, and thus the control of fluids and fluid pressure through the phacoemulsification handpiece, is critical to the procedure performed. Different medically recognized techniques have been utilized to control the fluid flow during the lens removal portion of the surgery. Among these, one popular technique is a simultaneous combination of phacoemulsification, irrigation and aspiration using a single handpiece. This method includes making the incision, inserting the handheld surgical implement to emulsify the cataract or eye lens, and, simultaneously with this emulsification, having the handpiece provide a fluid for irrigation of the emulsified lens and a vacuum for aspiration of the emulsified lens and inserted fluids.

Currently available phacoemulsification systems, such as those mentioned above, typically include a variable speed peristaltic pump and/or vacuum pump, a vacuum or pressure sensor, an adjustable source of ultrasonic power, and a programmable microprocessor with operator-selected presets for controlling aspiration rate, vacuum and ultrasonic power levels. The phacoemulsification handpiece is interconnected with a control console by an electric cable for powering and controlling a piezoelectric transducer that drives the action of the handpiece. Tubing provides irrigation fluid to the eye through the handpiece and enables withdrawal of aspiration fluid from an eye through the handpiece.

Generally, irrigation and aspiration are employed by the surgeon using the device to remove unwanted tissue and maintain pressure within the eye. Moreover, the use of, and particularly the pressurization of, the irrigation fluid is critical and may, for example, prevent the collapse of the eye during the removal of the emulsified lens. Irrigation fluid pressure is also used to protect the eye from the heat generated by the ultrasonic cutting needle and may suspend fragments created during the surgery in fluid for more easy removal through aspiration.

Irrigation fluid pressure has been conventionally handled in two ways. The first method to increase irrigation fluid pressure has relied upon the height of the fluid source. Conventional IV poles may be adjusted in height to create the desired pressure head using gravity-feed principles. The second method includes the use of an infusion pump either directly pumping the fluid typically in the form of a peristaltic pump used in-line with an irrigation delivery line or by pressurizing the fluid container thus increasing higher atmosphere above the fluid resulting in higher infusion pressure and flow to the surgical site.

Although each of the foregoing methods produces pressurized irrigation fluid at the surgical site, each suffers from difficulties in maintaining a constant pressure. For example, infusion pumps must be deployed with a dynamic pressure-sensing control loop to prevent over or under pressurizing the anterior chamber, and may further require venting to control unwanted pressures. Solving these issues may require the use of a special drip spike, a mechanical pressurization compartment, or an over-bag, to control atmospheric pressure. Such solutions add costs and complications to the surgical set-up and to the maintenance of the surgical equipment.

Thus, there is a need for a system and method that provides improved pressurized delivery of irrigation fluid to a surgical site.

SUMMARY OF THE INVENTION

The present disclosure is directed to a system and a method of providing pressurized fluid to the eye. The system and method may include at least one constant pressure source and at least one height adjustable irrigation fluid source to provide a stable pressurized fluid flow.

In one embodiment, a secondary set of fluidics lines are provided to allow phacoemulsification, irrigation and aspiration handpieces to be primed and ready for surgery simultaneously. A tertiary peristaltic pump and an additional fluid reservoir may be provided to pressurize a balanced salt solution (BSS) bag. The system software, tangibly embodied in hardware, would allow a surgeon to select a desired intraocular pressure and would then control the pumps and valves to achieve and maintain the selected pressure.

In one embodiment, the present invention provides a system for providing stable and pressurized flow of fluid during phacoemulsification surgery, the system comprising a supply source, a transfer reservoir communicatively coupled to the supply source via a twistable seal, a surgical console communicatively coupled to a pressurization port of the transfer reservoir, the surgical console having at least one system bus communicatively connected to at least one computing processor capable of accessing at least one computing memory associated with the at least one computing processor, and a surgical hand piece having at a distal end at least one surgical tool and at a proximal end being communicatively connected to at least one tube connected to an aperture of the transfer reservoir, wherein the pressurization port applies pressure to the transfer reservoir causing the modification of fluid flow through the at least one tube.

In one embodiment, the present invention comprises a system for providing stable and pressurized flow of fluid during phacoemulsification surgery, the system comprising, a supply source, a transfer reservoir communicatively coupled to the supply source via a spike, a surgical console communicatively coupled to a pressurization port of the transfer reservoir, the surgical console having at least one system bus communicatively connected to at least one computing processor capable of accessing at least one computing memory associated with the at least one computing processor, a surgical hand piece having at a distal end at least one surgical tool and at a proximal end being communicatively connected to at least one tube connected to an aperture of the transfer reservoir, wherein the pressurization port applies pressure to the transfer reservoir causing the modification of fluid flow through the at least one tube.

In one embodiment, the present invention comprises an apparatus for providing stable and pressurized flow of fluid during phacoemulsification surgery, the apparatus comprising, a supply source, a transfer reservoir communicatively coupled to the supply source via a spike, a surgical console communicatively coupled to a pressurization port of the transfer reservoir, the surgical console having at least one system bus communicatively connected to at least one computing processor capable of accessing at least one computing memory associated with the at least one computing processor, a surgical hand piece having at a distal end at least one surgical tool and at a proximal end being communicatively connected to at least one tube connected to an aperture of the transfer reservoir, wherein the pressurization port applies pressure to the transfer reservoir causing the modification of fluid flow through the at least one tube.

Accordingly, the disclosure provides a system and method that provides improved pressurized delivery of irrigation fluid to a surgical site.

DESCRIPTION OF THE DRAWINGS

The accompanying drawings are included to provide a further understanding of the invention, and are incorporated in and constitute a part of this specification. The drawings illustrate disclosed embodiments and/or aspects and, together with the description, serve to explain the principles of the invention, the scope of which is determined by the claims.

In the drawings.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in typical surgical, and particularly optical surgical, apparatuses, systems, and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

Pressurized infusion may be used for maintaining stability in the anterior chamber of the eye during phacoemulsification. Stable eye pressure may be critical to prevent damage to the eye during cataract surgery and may help speed the surgical process. However, many existing types of balanced salt solution (BSS) containers, such as "IVs", lack the means to be pressurized and instead are designed for gravity fed fluid delivery. In an embodiment of the present invention, a BSS source capable of acting as a pressurized irrigation source, such as an IV bag/bottle, may be added to an existing BSS source without contaminating the fluid available for surgical use. As would be appreciated by those skilled in the art, in addition to being operable with various other liquids besides BSS, the present invention is operable with any type of container which may be used in a surgical setting which is equipped with at least one orifice as described herein.

Figure 1:
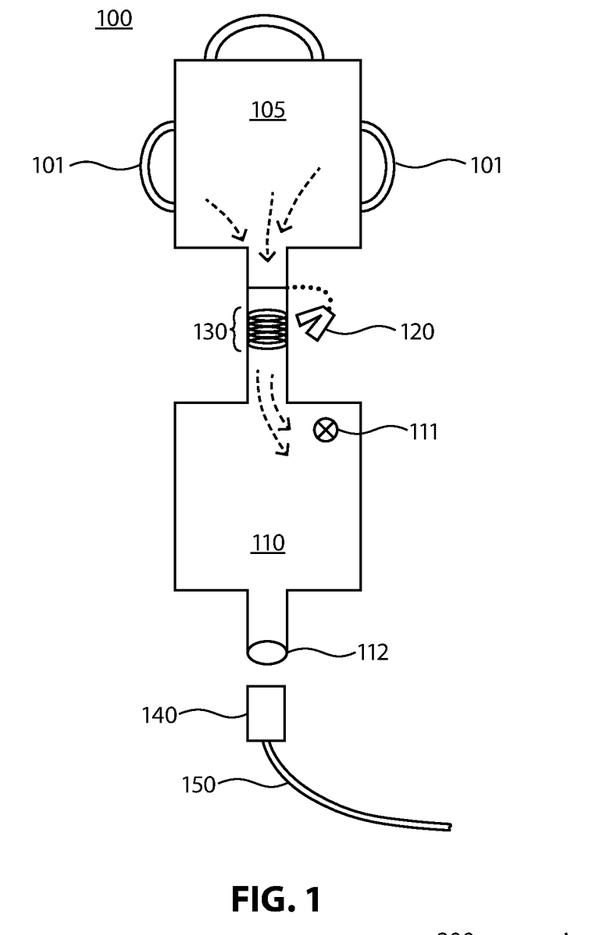
FIG. 1 illustrates an embodiment of the reservoir apparatus of the present invention.

As illustrated in FIG. 1, system 100 may comprise a supply source 105 which may be communicatively coupled to transfer reservoir 110. The union between the primary supply source 105 and transfer reservoir 110, which may comprise seal 130 and clamp 120, may be pliable and may accommodate various types of IV bags/bottles. For example, supply source 105 may take the form of a bag or bottle and may be any container known to be used for providing irrigation fluids. Supply source 105 may also have associated therewith handles or hanger apparatus 101 to more easily allow connection with a pole or other device used with a phacoemulsification surgical system. Supply source 105 may preferably take the form of a rigid bottle.

Pressure may be supplied to transfer reservoir 110 through pressure port 111 which may allow for the delivery of pressurized fluid through line 150. Attachment means 140 may take the form of a spike and may be received at a bottom port 112 associated with transfer reservoir 110 to allow for the flow of fluid to a surgical system. Bottom port 112 may be capped or include a stopper assembly which may accept, for example, a spike. As would be appreciated by those skilled in the art, pressure port 111 may accept any pressure desired by the user up to a maximum available pressure, and may use air or any specific gas to provide the increase or modification in pressure in at least the transfer reservoir 110.

Figure 2:
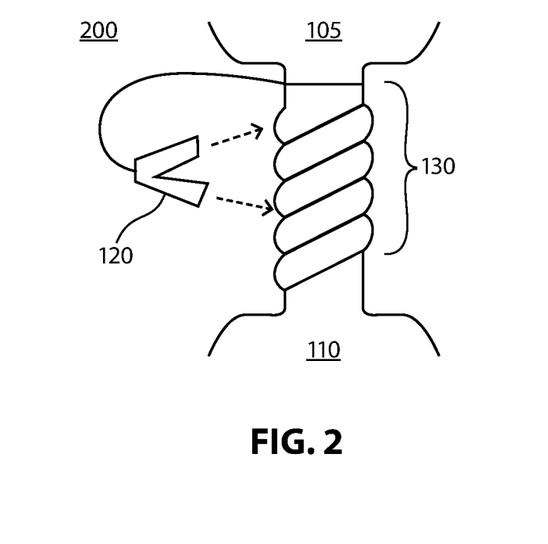
FIG. 2 illustrates an embodiment of the reservoir apparatus of the present invention.

The supply source 105 may be connected to transfer reservoir 110 by seal 130 which may be a pliable, non-porous plastic, providing a water and air tight seal connection. As illustrated in FIG. 2, system 200 may comprise seal 130 which may be in the form of a sleeve and may be twistable to substantially close the passage formed by seal 130 between supply source 105 and transfer reservoir 110. Seal 130 may also be sealed by the use of clamp 120, which may be used on an at least partially twisted or non-twisted seal 130. The closure of seal 130 may allow for controlled pressurization of transfer reservoir 110 and may, upon at least partial release, allow fluid to flow from supply source 105 to transfer reservoir 110 during a surgical procedure. This may allow for the continued availability of BSS, for example, without having to disturb the mating of attachment means 140 to transfer reservoir 110.

Figure 3:
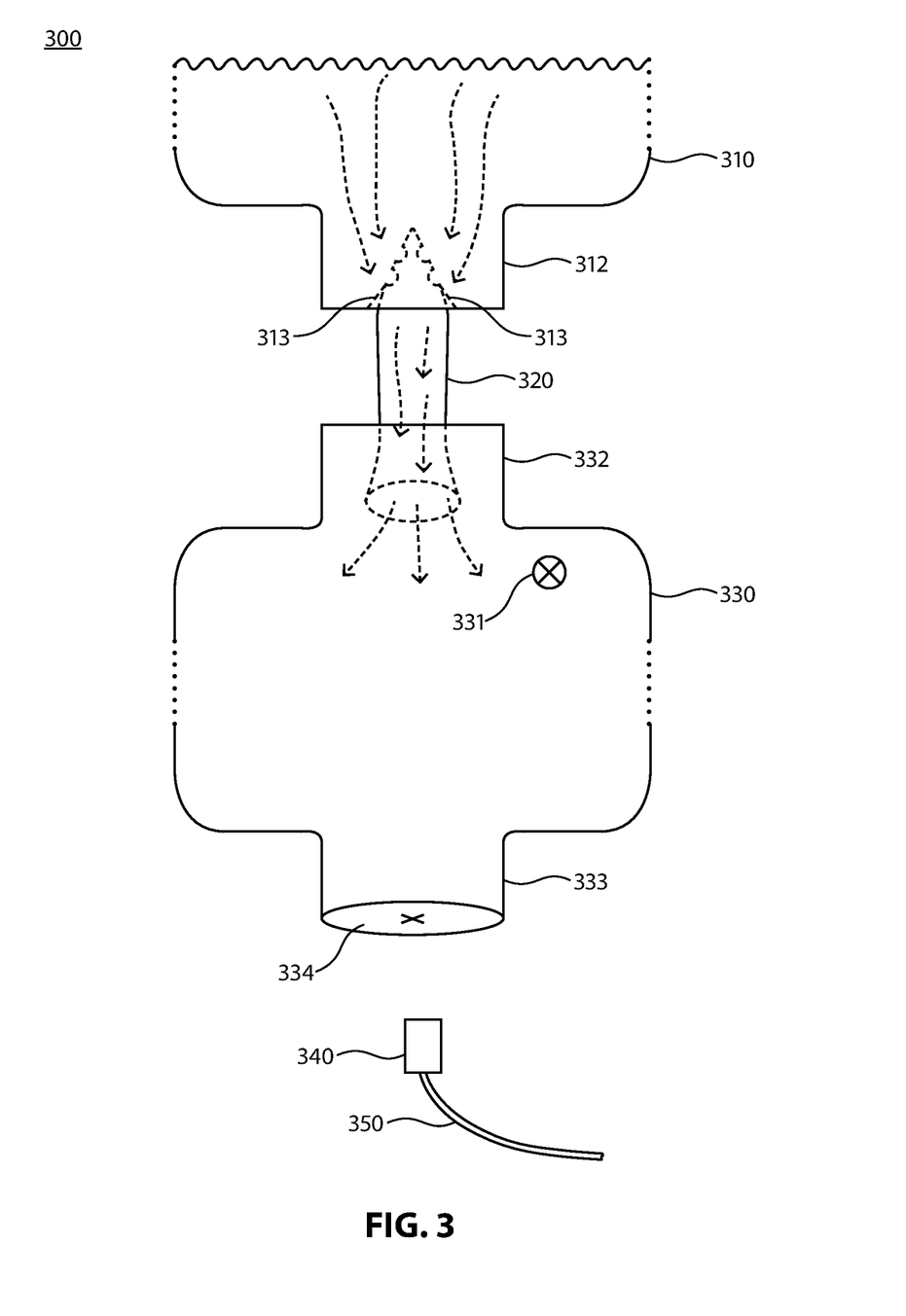
FIG. 3 illustrates an embodiment of the reservoir apparatus of the present invention.

In an embodiment of the present invention, as illustrated in FIG. 3, a spike 320 may be employed to communicatively connect reservoir 310 with reservoir 330 of system 300. Spike 320 may be permanently affixed to reservoir 330 and may be sufficiently stabilized within port 332 to allow for spike 320 to be forced through port 312, such as by the force applied by a user of the present invention. In this way, reservoir 330 and spike 320 may be a single unit and may include, for example, a cap, wrapper or other covering on at least a portion of spike 320 to preserve sterility of the reservoir 330. In an embodiment of the present invention, reservoir 310 supplies BSS via spike 320 to reservoir 330 which may be substantially empty prior to communicatively coupling with reservoir 310. Alternatively, reservoir 330 may be pre-loaded with BSS, for example, and may be of any size as would be appreciated by those skilled in the art.

In an embodiment of the present invention, spike 320 may be removeably affixed to reservoir 330 and may be otherwise attached by a user to any reservoir having a suitable aperture. Spike 320 may also comprise at least one flange 313 which may be used to enhance the stability and integrity of the connection with another reservoir. Flange 313 may be flexible and may, for example, deflect towards the body of spike 320 when being inserted through an aperture and may regain normality once through the aperture to provide at least one additional contact point between the port 312 and the spike 320. A plurality of flanges may be used. Similarly, each flange may be of any useful shape and may preferably have a rounded bottom edge so as to not damage any portion of port 312.

Reservoir 310 may be an existing reservoir that is not suitable for pressurized infusion or may be a reservoir such as reservoir 330 with or without spike 320. In this way, multiple reservoirs may be interconnected as needed through, for example, port 333 through aperture 334. A similar port configuration may be used with any of the reservoirs discussed herein as would be appreciated by those skilled in the art. Reservoir 330 may also include a pressurization port 331, which may suitably receive pressure from a surgical console to increase the pressure within at least reservoir 330. Fluid from reservoir 330 may flow to surgical site through tube 350 which may be joined to reservoir 330 by way of attachment means 340, which may, for example, be a spike or other apparatus capable of communicatively connecting a tube to a fluid source.

Figure 4:
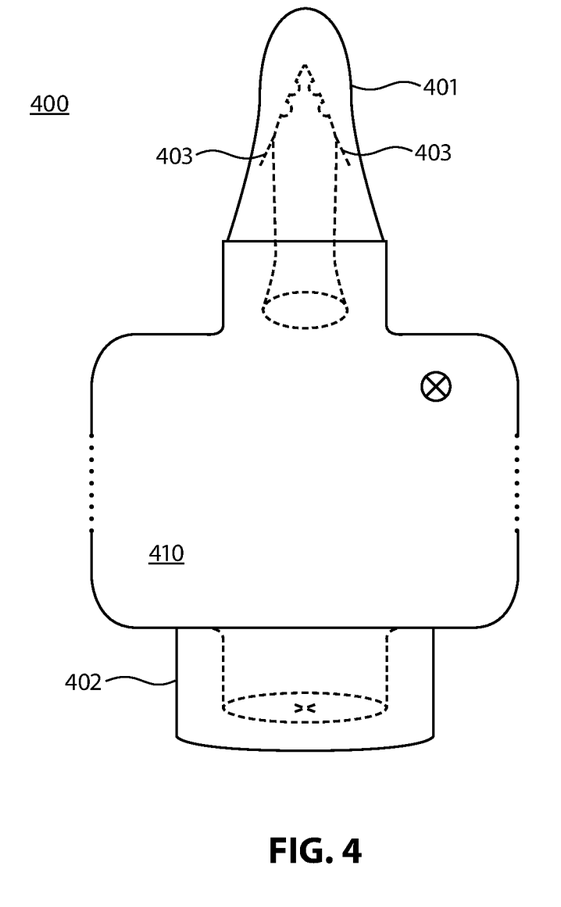
FIG. 4 illustrates an embodiment of the reservoir apparatus of the present invention.

As discussed above, and as more fully illustrated in FIG. 4, a reservoir of the present invention may include at least one spike and may include protective coverings to maintain sterility prior to use. For example, apparatus 400 may include reservoir 410 which may include at least one port and at least one spike (each shown in dashed form) each with its own covering. A spike associated with reservoir 410 may be temporarily covered by cap 401 and a port associated with reservoir 410 may be covered by cap 402. As discussed above, the spike may include at least on flange 403 to enhance attachment to a receiving reservoir. Each cap may provide a hermetic seal around the spike and/or port(s) located on the reservoir 410 and may be removable without damaging any aspect of the reservoir system 400. As would be understood by those skilled in the art, the caps may be adhered to the body of reservoir 410 through the use of adhesives, for example, and may also be mechanically attached.

Figure 5A:
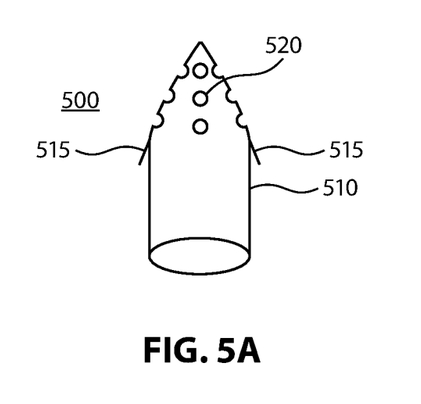
FIGS. 5A and 5B illustrate embodiments of a spike of the present invention.
Figure 5B:
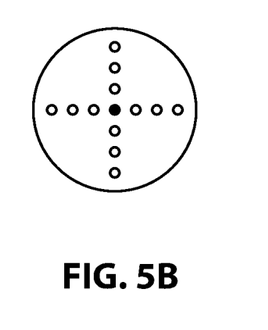

Various spike shapes and configurations may be used with the present invention to provide greater ease of conjoining at least two reservoirs and for providing different rates of fluid flow through at least one spike. For example, as illustrated in FIG. 5A, a top portion of a spike as illustrated as body 500 may have a cylindrical lower portion 510 and have a narrowing top portion terminating in at a single point suitable to allow at least a portion of body 500 to penetrate a reservoir through a port associated therewith. The top portion of body 500 may comprise a plurality of openings 520 suitable for allowing for fluid to flow through the body 500 as well as attachment means 515, which may provide increased stability of the body 500 when inserted into a port, for example. As illustrated in both FIGS. 5A and 5B (which offers a top view of body 500), the openings may be uniformly dispersed within the top portion of body 500 to provide for a uniform flow. In alternative embodiment, the openings may be of any size and/or shape and be formed in any suitable pattern.

Figures 6, 7A, 7B, 7C, 7D:
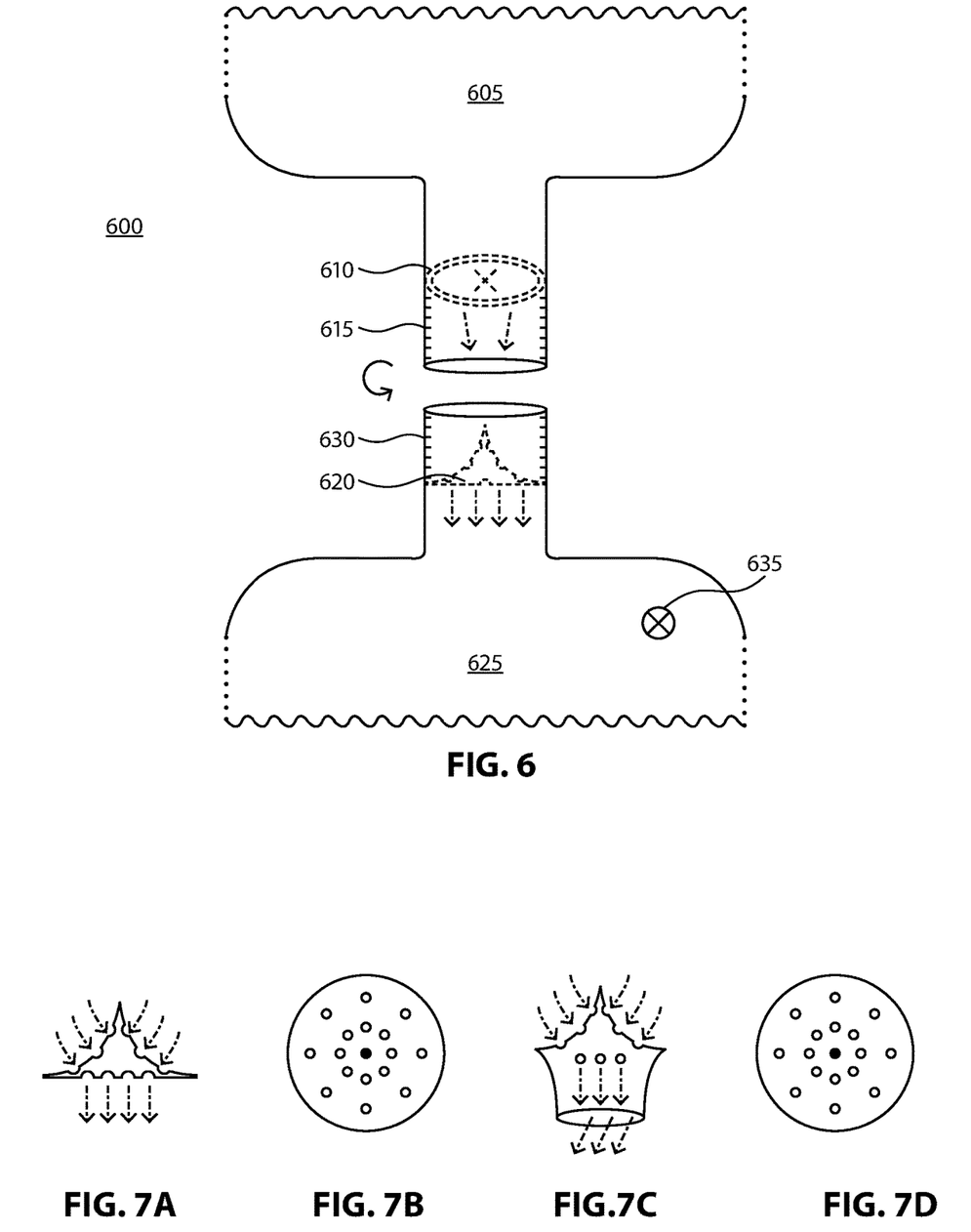
FIG. 6 illustrates an embodiment of the reservoir apparatus of the present invention.
FIGS. 7A-D illustrate embodiments of a spike of the present invention.

In an embodiment of the present invention, two reservoirs having recessed attachment means may be conjoined. As illustrated in FIG. 6 by system 600, for example, reservoir 605 may comprise a port 610 located at the bottom of reservoir 605 and may be recessed into seal membrane 615. Similarly, reservoir 625 may include a spike 620 near the top of the reservoir 625 recessed below the top of flexible seal membrane 630.

The seal membranes may be flexible, semi-flexible, semi-rigid, and/or rigid. Semi-rigid and rigid membranes may also comprise attachment means such as, for example, male and/or female screw threads which may allow the membranes to at least partially mechanically attach the mating reservoirs together. A screw based attachment means may also provide sufficient force to allow a spike associated with one reservoir to at least partially penetrate a port of another reservoir. If the seal membrane is flexible or semi-flexible, for example, two reservoirs may be forced together to sufficiently seat the spike of one reservoir substantially into a receiving port. In such a configuration, the one or both of the spike/port or seal membrane(s) combinations may provide mechanical support to keep the two reservoirs fluidly connected to each other.

In an embodiment of the present invention, system 600 may comprise reservoir 605 together fluidly connected with reservoir 625. The fluid connection may further comprise a screw based attachment means associated with each of seal membrane 630 and seal membrane 615, which may allow each of the reservoirs to be drawn together in a manner which provides sufficient force to allow spike 620 to at least partially penetrate port 610 to allow for reservoir 605 to be fluidly connected to reservoir 625. Pressure may be introduced into system 600 through pressure port 635.

A variety of known and novel spikes may be used with the present invention. For example, as illustrated in FIGS. 7A-B, a low-profile spike may be used which may include a narrow vertical profile which may ease the resistance between the spike and a port. Similarly, a spike, such as that illustrated in FIGS. 7C-D, may comprise a more pronounced body which may control fluid flow, for example, and may provide a shape which may provide a more firm mating with a portal.

Those of ordinary skill in the art may recognize that many modifications and variations of the herein disclosed systems and methods may be implemented without departing from the spirit or scope of the invention. Thus, it is intended that the present invention covers such modifications and variations provided they come within the scope the appended claims and their equivalents.

What is claimed is:

1. A system for providing stable and pressurized flow of infused fluid during phacoemulsification surgery, the system comprising
- a supply source;
- a clamp;
- a transfer reservoir comprising a pressurization port and an aperture, the transfer reservoir being communicatively coupled to the supply source via a seal;
- the seal comprising a twistable sleeve and a passage within the twistable sleeve, the passage being between the supply source and the transfer reservoir, the twistable sleeve being configured to twist in a first direction or in a second direction that is opposite the first direction to adjust a closure of the passage, the clamp being configured to be on a twistable portion of the twistable sleeve when the twistable sleeve is at least partially twisted or non-twisted;
- an attachment piece configured to communicatively connect at least one tube to the aperture of the transfer reservoir;
- wherein pressure is provided through the pressurization port to the transfer reservoir causing the stable and pressurized flow of the infused fluid through the at least one tube.

2. The system of claim 1, wherein the twistable sleeve proportionally controls the stable and pressurized flow of the infused fluid by being in a partially twisted state or a non-twisted state.

3. The system of claim 1, wherein the transfer reservoir is pre-loaded with a balanced salt solution.

4. The system of claim 1, wherein the seal is configured to provide a water and air tight seal connection between the supply source and the transfer reservoir.

5. The system of claim 1, wherein the twistable sleeve is configured to control pressurization of the transfer reservoir by being twisted to adjust a closure of the passage formed by the seal.

6. The system of claim 1, wherein the twistable sleeve is configured to control the infused fluid flow from the supply source to the transfer reservoir during a surgical procedure by being twisted to adjust a closure of the passage formed by the seal.

7. The system of claim 1, wherein the seal is configured to provide continued availability of a balanced salt solution of the transfer reservoir without disturbing the attachment piece.

8. The system of claim 1, wherein a pressure source provides the pressure through the pressurization port to the transfer reservoir.

9. The system of claim 1, wherein the seal comprises a pliable, non-porous plastic material.

10. An apparatus for providing stable and pressurized flow of infused fluid during phacoemulsification surgery, the apparatus comprising:
- a supply source;
- a transfer reservoir comprising a pressurization port and an aperture, the transfer reservoir being communicatively coupled to the supply source via a twistable seal;
- the twistable seal comprising a sleeve and a passage within the twistable sleeve, the passage being between the supply source and the transfer reservoir, the twistable sleeve being configured to twist in a first direction or in a second direction that is opposite the first direction to adjust a closure of the passage, the clamp being configured to be on a twistable portion of the twistable sleeve when the twistable sleeve is at least partially twisted or non-twisted;
- an attachment piece configured to communicatively connect at least one tube to the aperture of the transfer reservoir;
- wherein pressure is provided through the pressurization port to the transfer reservoir causing the stable and pressurized flow of the infused fluid through the at least one tube.

11. The apparatus of claim 10, wherein the twistable seal proportionally controls the stable and pressurized flow of the infused fluid by being in a partially twisted state or a non-twisted state.

12. The apparatus of claim 10, wherein the transfer reservoir is pre-loaded with a balanced salt solution.

* * * * *